United States Patent
Derenne et al.

(10) Patent No.: US 10,410,500 B2
(45) Date of Patent: Sep. 10, 2019

(54) PERSON SUPPORT APPARATUSES WITH VIRTUAL CONTROL PANELS

(71) Applicant: Stryker Corporation, Kalamazoo, MI (US)

(72) Inventors: Richard A. Derenne, Portage, MI (US); Ammon K. Wright, Portage, MI (US); Richard Thomas DeLuca, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 567 days.

(21) Appl. No.: 14/549,006

(22) Filed: Nov. 20, 2014

(65) Prior Publication Data

US 2015/0077534 A1   Mar. 19, 2015

Related U.S. Application Data

(63) Continuation-in-part of application No. 13/242,022, filed on Sep. 23, 2011, now Pat. No. 9,204,823.
(Continued)

(51) Int. Cl.
*G08B 21/04* (2006.01)
*H04N 7/18* (2006.01)
(Continued)

(52) U.S. Cl.
CPC .......... *G08B 21/0476* (2013.01); *A61B 5/002* (2013.01); *A61B 5/0013* (2013.01); *A61B 5/1113* (2013.01); *A61B 5/1128* (2013.01); *A61B 5/7445* (2013.01); *G06F 3/017* (2013.01); *G06F 3/0416* (2013.01);
(Continued)

(58) Field of Classification Search
CPC ..... A61B 5/0013; A61B 5/002; A61B 5/1113; A61B 5/1115; A61B 5/1117; A61B 5/1123; A61B 5/1128; A61B 5/6889; A61B 5/6892; A61B 5/7445; A61B 5/7475; G06F 19/30; G06F 3/017; G06F 3/0416
See application file for complete search history.

(56) References Cited

U.S. PATENT DOCUMENTS 8,356,254 B2   1/2013 Dennard et al.
8,952,894 B2 * 2/2015 Wilson ................. G06F 3/0304
345/156

(Continued)

*Primary Examiner* — Peter D Le
(74) *Attorney, Agent, or Firm* — Warner Norcross + Judd LLP

(57) ABSTRACT

A virtual control panel for a person support apparatus includes at least one image sensor that monitors a movement of a user's finger(s) relative to a control surface. The control surface includes one or more control images thereon. When the user's finger(s) move within a threshold distance of the control image, a controller reacts as if the user had pushed an actual control button for the function that corresponds to the control image. The control image may be projected by a projector, and may have static or dynamic content. Alternatively, the control image may be printed on the surface, adhered thereto, or otherwise physically present. In some embodiments, ancillary devices may connect to the person support apparatus and forward images for projection on the control surface, thereby allowing the control surface of the person support apparatus to be used to control the ancillary devices.

18 Claims, 6 Drawing Sheets

Related U.S. Application Data

(60) Provisional application No. 61/385,607, filed on Sep. 23, 2010.

(51) Int. Cl.
  *G06F 3/01* (2006.01)
  *G06F 3/041* (2006.01)
  *H04N 5/33* (2006.01)
  *A61B 5/00* (2006.01)
  *A61B 5/11* (2006.01)
  *G08B 21/24* (2006.01)
  *G16H 40/63* (2018.01)
  *G06F 19/00* (2018.01)

(52) U.S. Cl.
  CPC ......... *G08B 21/043* (2013.01); *G08B 21/245* (2013.01); *G16H 40/63* (2018.01); *H04N 5/33* (2013.01); *H04N 7/181* (2013.01); *H04N 7/185* (2013.01); *A61B 5/1115* (2013.01); *A61B 5/1117* (2013.01); *A61B 5/1123* (2013.01); *A61B 5/6889* (2013.01); *A61B 5/6892* (2013.01); *A61B 5/7475* (2013.01); *G06F 19/30* (2013.01)

(56) References Cited

U.S. PATENT DOCUMENTS

| | | | | |
|---|---|---|---|---|
| 9,298,318 | B2* | 3/2016 | Morrison | G06F 3/0425 |
| 9,593,833 | B2 | 3/2017 | McMannon et al. | |
| 2003/0052787 | A1* | 3/2003 | Zerhusen | A47B 23/046 |
| | | | | 340/573.1 |
| 2005/0168448 | A1* | 8/2005 | Simpson | G06F 3/0418 |
| | | | | 345/173 |
| 2006/0077186 | A1* | 4/2006 | Park | G06F 3/0412 |
| | | | | 345/173 |
| 2006/0080554 | A1* | 4/2006 | McDonald | G06F 21/6254 |
| | | | | 713/189 |
| 2006/0181776 | A1* | 8/2006 | Sandhu | G02B 27/024 |
| | | | | 359/618 |
| 2008/0018591 | A1* | 1/2008 | Pittel | G06F 1/1616 |
| | | | | 345/156 |
| 2008/0172789 | A1* | 7/2008 | Elliot | A61G 7/0528 |
| | | | | 5/616 |
| 2009/0091458 | A1* | 4/2009 | Deutsch | G06F 19/327 |
| | | | | 340/573.1 |
| 2009/0100599 | A1* | 4/2009 | Rawls-Meehan | A47C 20/041 |
| | | | | 5/616 |
| 2009/0112541 | A1* | 4/2009 | Anderson | G09B 19/0076 |
| | | | | 703/11 |
| 2009/0119843 | A1* | 5/2009 | Rodgers | A61B 5/1115 |
| | | | | 5/611 |
| 2009/0262098 | A1* | 10/2009 | Yamada | G06F 1/1616 |
| | | | | 345/175 |
| 2010/0295823 | A1* | 11/2010 | Ahn | G06F 3/0425 |
| | | | | 345/175 |
| 2011/0140869 | A1* | 6/2011 | Liu | A61G 7/018 |
| | | | | 340/286.07 |
| 2012/0075464 | A1 | 3/2012 | Derenne et al. | |
| 2012/0110516 | A1 | 5/2012 | Tumanov | |
| 2012/0116803 | A1* | 5/2012 | Reid | A61L 2/28 |
| | | | | 705/2 |
| 2012/0212582 | A1* | 8/2012 | Deutsch | G08B 21/245 |
| | | | | 348/46 |
| 2013/0050069 | A1 | 2/2013 | Ota | |
| 2013/0239041 | A1 | 9/2013 | DaCosta | |
| 2014/0259410 | A1 | 9/2014 | Zerhusen et al. | |
| 2015/0268739 | A1 | 9/2015 | Sanaullah et al. | |

* cited by examiner

PERSON SUPPORT APPARATUSES WITH VIRTUAL CONTROL PANELS

CROSS-REFERENCE TO RELATED APPLICATIONS

This application is a continuation-in-part application of U.S. patent application Ser. No. 13/242,022 filed Sep. 23, 2011 by inventors Richard A. Derenne et al. and entitled VIDEO MONITORING SYSTEM, which in turn claims priority to U.S. provisional patent application Ser. No. 61/385,607 filed Sep. 23, 2010, by inventors Richard A. Derenne et al. and entitled VIDEO MONITORING SYSTEM, the complete disclosures of both of which are incorporated herein by reference.

BACKGROUND OF THE INVENTION

The present invention relates to person support apparatuses, such as beds, cots, stretchers, operating tables, recliners, or the like. More specifically, the present invention relates to person support apparatuses that include one or more control panels for controlling various aspects of the person support apparatus. Many person support apparatuses include control panels for changing the configuration of the person support apparatus, such as changing the height of a support surface, changing an orientation of the support surface, operating a brake, etc. Such control panels typically include a plurality of buttons with electrical switches that detect when the button is pushed, and/or one or more touch screens that detect the location and context of a user touching the screen.

SUMMARY OF THE INVENTION

According to at least one aspect, the present invention provides a virtual control panel for a person support apparatus that is easy to clean and disinfect, thereby reducing the risk of infectious materials being passed from one person to another. In other aspects, a virtual control panel is provided having dynamic controls, thereby enabling the controls of the virtual control panel to change. In still other aspects, the person support apparatus and virtual control panel are configured to allow an ancillary device to connect to the person support apparatus. The ancillary device forwards images to the virtual control panel for projection on the control surface, thereby allowing the control surface of the person support apparatus to be used to control the ancillary device. Other aspects of the present invention are described below.

According to one embodiment, a person support apparatus is provided that includes a frame, a support, an actuator, a surface, an image projector, an image sensor, and a controller. The support supports a person thereon. The actuator moves a component of the person support apparatus when actuated. The image projector projects a control image onto the surface. The image sensor captures images of a user's finger when positioned near the surface. The controller analyzes images from the image sensor and determines if the user has moved a finger within a threshold distance of a location on the surface at which the control image is located and, if so, the controller actuates the actuator.

According to other aspects, the threshold distance is zero and the controller determines if the user has touched the location on the surface at which the control image is located before actuating the actuator.

In other aspects, the image sensor comprises both an optical camera and an infrared detector. The infrared detector determines if the user's finger has moved within the threshold distance of the location on the surface at which the control image is located. In still other embodiments, the person support apparatus also includes an infrared light source that projects a beam of infrared light along a plane that is generally parallel to the surface and spaced from the surface the threshold distance. The infrared detector detects reflections of the infrared light when the user's finger intersects the infrared light.

In still other aspects, the person support apparatus is a bed having a footboard and the image projector and image sensor are both positioned at the footboard. In another aspect, the person support apparatus is a bed having a plurality of siderails and the image projector and image sensor are both positioned at one or both of the siderails.

The person support apparatus also includes, in at least some embodiments, at least a second image projector. The second image projector projects a second control image onto the surface that is superimposed on the control image. The second projector may be positioned on a different side of the control image than the first projector so that, in the event an object blocks projection of the control image by the first projector, the control image will likely not be blocked by the second projector, thereby ensuring the control image does not disappear from view.

In other aspects, the controller is adapted to actuate the actuator for as long as the user's finger remains within the threshold distance of the location on the surface at which the control image is located, and to de-actuate the actuator when the user's finger moves outside of the threshold distance of the location on the surface at which the control image is located. The actuator may be adapted to change a height of the support, or to change an angle of the support, or to pivot a first section of the support with respect to a second section of the support, or to carry out still other movement.

According to another embodiment, a person support apparatus is provided that includes a frame, a support, a surface, an image sensor, and a controller. The support supports a person thereon. The surface includes a user interface image thereon that includes a first control image and a second control image. The image sensor captures images of a user's finger when positioned near the surface. The controller analyzes images from the image sensor and determines if the user has moved a finger within a threshold distance of a first location on the surface or a second location on the surface. The first location corresponds to a location at which the first control image is located and the second location corresponds to a location at which the second control image is located. The controller also controls the person support apparatus in a first manner if the user has moved his or her finger within the threshold distance of the first location and controls the person support apparatus in a second manner if the user has moved his or her finger within the threshold distance of the second location.

In other aspects, the first and second control images are printed on the surface.

In still other aspects, the person support apparatus includes an image projector that projects the first and second control images onto the surface.

In some embodiments, the first manner includes moving a component of the person support apparatus in a first direction and the second manner includes moving the component in a second direction opposite to the first direction.

In other embodiments, the first manner includes activating an exit alert system that issues an alert if an occupant of the person support apparatus exits, and the second manner includes deactivating the exit alert system.

In still other embodiments, the first manner includes ceasing to project the user interface image onto the surface and projecting a different user interface image onto the surface, the different user interface image including a third control image. The controller may also be adapted to analyze the images from the image sensor to determine if the user has moved a finger within the threshold distance of a third location on the surface wherein the third location corresponds to a location at which the third control image is located.

The person support apparatus, in at least some embodiments, also includes an ambient light sensor in communication with the controller. The controller alters an intensity at which the image projector projects the user interface image onto the surface in response to an output of the ambient light sensor.

In still other embodiments, the person support apparatus includes a sensor adapted to detect the presence of an authorized individual in proximity to the person support apparatus and the controller projects the user interface image when the authorized individual is in proximity to the person support apparatus and stops projecting the user interface image when the authorized individual is not in proximity to the person support apparatus.

The image sensor comprises both an optical camera and an infrared detector, in at least some embodiments, and the infrared detector is adapted to determine if the user's finger has moved within the threshold distance of either of the first and second locations. The image sensor may further include an infrared light source adapted to project a beam of infrared light along a plane that is generally parallel to the surface and spaced from the surface the threshold distance. The infrared detector detects reflections of the infrared light when the user's finger intersects the infrared light.

According to another embodiment, the person support apparatus also includes a second image projector adapted to project the user interface image onto a second surface, a second image sensor adapted to capture images of the user's finger when positioned near the second surface, and a second controller. The second controller analyzes images from the second image sensor and determines if the user has moved a finger within the threshold distance of the user interface image on the second surface. The second controller also controls the person support apparatus in at least one of the first and second manners if the user has moved his or her finger within the threshold distance of the user interface on the second surface. The second controller is, in some embodiments, in communication with the first controller.

According to still another embodiment, a person support apparatus is provided that includes a frame, a support, a first surface, a second surface, a first image projector, a second image projector, a first image sensor, a second image sensor, and first and second controllers. The first image projector projects a first image onto the first surface. The second image projector projects a second image onto the second surface. The first image sensor captures images of a user's finger when positioned near the first surface. The second image sensor captures images of a user's finger when positioned near the second surface. The first controller analyzes images from the first image sensor and determines if the user has moved a finger within a threshold distance of the first image. The second controller analyzes images from the second image sensor and determines if the user has moved a finger within a threshold distance of the second image. The first and second controllers are in communication with each other.

According to still other aspects, the second projector stops projecting the second image onto the second surface when the user moves his or her finger within the threshold distance of a first point on the first surface over which the first image is projected. The first image may include a lockout control image that is projected onto the first point on the first surface.

The second projector projects a third image onto the second surface when the user moves his or her finger within the threshold distance of a first point on the first surface on which the first image is projected, in at least some embodiments.

In some embodiments, the person support apparatus is a bed having a footboard and a plurality of siderails and the first image projector and first image sensor are both positioned at the footboard, and the second image projector and the second image sensor are both positioned at one of the siderails. The first and second controllers communicate with each other over a communications network.

According to still other aspects, a video monitoring system is provided that includes at least one video camera, a projector, and a computer device. The projector projects an image of a control panel having one or more control images thereon. The video camera captures video images and outputs signals representative of the video images to the computer device. The computer device processes the signals to determine if a person has moved any of his or her fingers, arms, or other body parts, in a manner that touches any of the control images, or otherwise comes within a threshold distance of any of the control images.

One or more of the video cameras used in the system may include, in addition to the ability to record digital images, the ability to sense distances from the camera to the objects or individuals that are positioned in the camera's field of view. Such depth sensing ability is based, in at least one embodiment, upon the projection of infrared light and the detection of reflections of that infrared light by sensors that are part of the system. The depth information is used in combination with the image information to determine the three dimensional position and/or movement of individuals and/or objects within the viewing field of the camera. In addition to, or as a replacement of the video camera, a thermal imaging camera may also be used.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
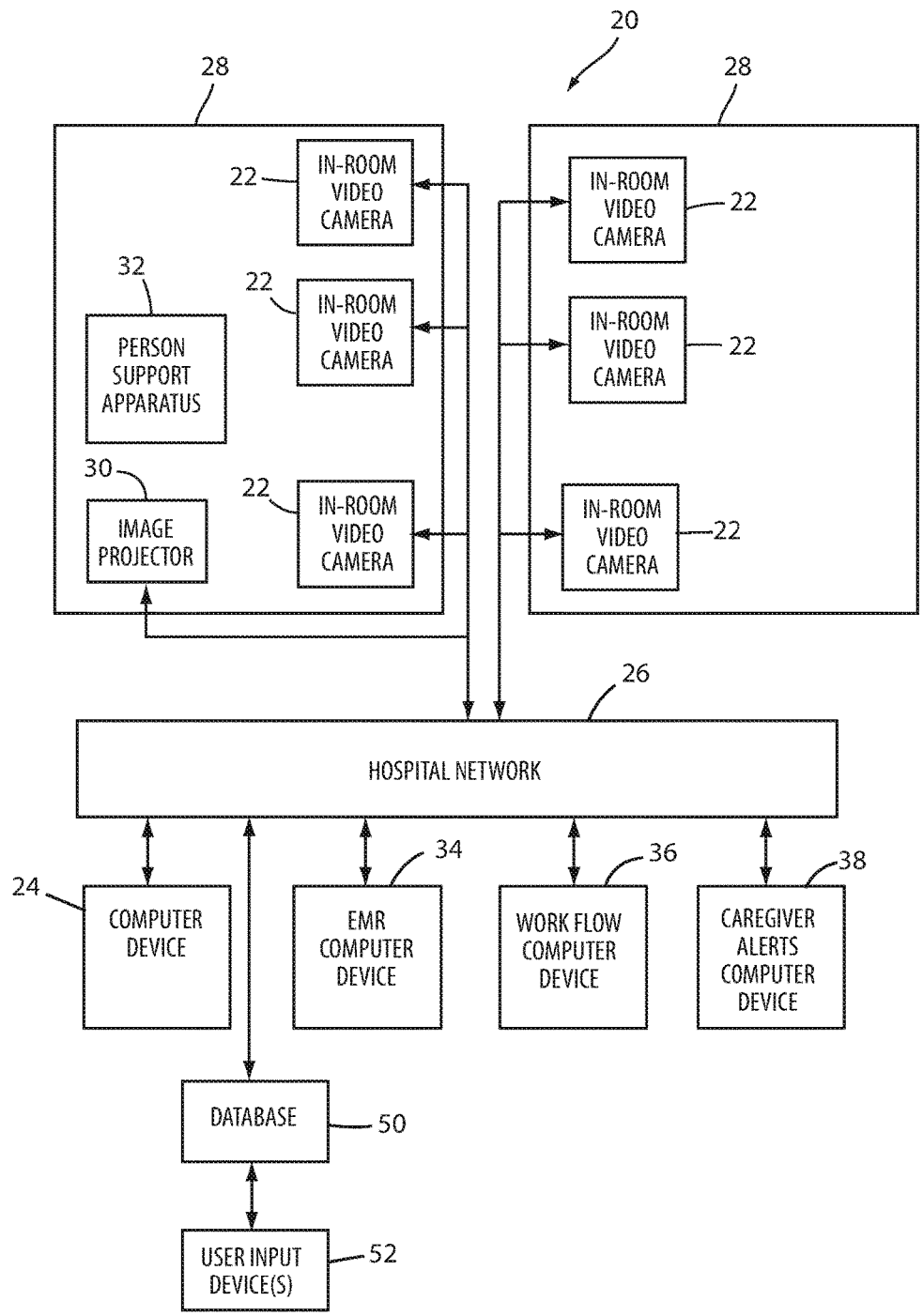
FIG. 1 is a block diagram of a video monitoring system according to a first embodiment of the invention.

A video monitoring system 20 according to a first embodiment of the invention is shown in FIG. 1. Monitoring system 20 includes one or more conventional video cameras 22 and/or other types of vision sensing or motion sensing equipment. Video monitoring system 20 is adapted to sense one or more actions undertaken by one or more persons in the room or other environment. The data gathered by the video monitoring system is processed by appropriate hardware and/or software to determine what action should be taken in response to movement of the one or more persons. Video monitoring system 20 is especially suitable for use in patient care environments—such as hospitals, nursing homes, medical facilities, etc.—where person support apparatuses, such as beds, stretchers, cots, chairs, recliners, operating tables, or other person support apparatuses are present.

Video monitoring system 20 includes, in addition to cameras 22, a computer device 24, a computer network 26, and one or more image projectors 30 positioned in one or more rooms 28. Depending on the particular facility in which video monitoring system 20 is implemented, computer network 26 may further include any one or more computer devices that are in communication with computer network 26, such as, but not limited to, an electronic medical records (EMR) computer device 34, a work flow computer device 36, and a caregiver alert computer device 38.

Projectors 30 are conventional projectors that are capable of projecting images onto a screen or any other type of surface. The images that are projected by projector 30 are controlled by one or more computers, such as computer device 24. The projected images include at least one image of a control panel that, as will be discussed in greater detail below, is used in conjunction with one or more cameras 22 to create a virtual control panel. The virtual control panel is used to control one or more aspects of a person support apparatus 32, one or more aspects of the room 28 in which the person is supported (e.g. television, radio, thermostat, curtains, etc.), and/or one or more aspects of a computer, server, or other electronic device in which the person support apparatus 32 is in communication, such as, but not limited to, any one or more of EMR computer device 34, work flow computer device 36, and/or caregiver alert computer device 38.

Computer device 24 is a conventional server that communicates with both cameras 22 and projectors 30 over network 26, in at least one embodiment. In other embodiments, computer device 24 includes one or more personal computers (PCs), or it is a dedicated electronic structure configured to carry out the logic and algorithms described herein, or any combination of these or other known devices capable of carrying out the logic and algorithms described herein. Such dedicated electronic structures include any combination of one or more processors, systems on chip (SoC), field programmable gate arrays (FPGA), microcontrollers, discrete logic circuitry, software and/or firmware. Regardless of whether computer device 24 is a single physical device, or is multiple physical devices working together (which may be located in different physical locations), computer device 24 represents the hardware, software and/or firmware necessary to carry out the algorithms described herein.

In one embodiment, video cameras 22 of system 20 are motion sensing devices sold under the brand name Kinect™, or variations thereof, by Microsoft Corporation of Redmond, Wash., USA. The Kinect™ motion sensing device includes an RGB (red, green, blue) camera, a depth sensor, and a multi-array microphone. This device is used to provide full-body 3D motion, facial recognition, and voice recognition capabilities. The depth sensor includes an infrared laser projector combined with a complementary metal oxide semiconductor (CMOS) sensor, which captures reflected signals from the laser projector and combines these signals with the RGB sensor signals. The Kinect™ motion sensing device automatically detects the position of one or more persons and outputs data indicating the locations of multiple body portions, such as various joints of the person, multiple times a second. Such information is then processed to determine any of the conditions discussed herein.

In other embodiments, any one or more of the video cameras 22 are a WAVI Xtion™ motion sensing system, or variations thereof, marketed by Asustek Computer, Inc., which has a principal place of business in Taipei, Taiwan. The WAVI Xtion™ motion sensing system uses one or more depth sensors to sense the position and movement of people without requiring the people to hold any objects.

In still other embodiments, other types of video cameras 22 are used, or a combination of one or more of the Kinect™ cameras 22 is used with one or more of the WAVI Xtion™ cameras 22. Still other combinations of cameras 22 are also possible. Modifications may also be made to the camera 22, whether it includes a Kinect™ camera or a WAVI Xtion™ camera, or some other camera, in order to carry out the functions described herein, as would be known to one of ordinary skill in the art. It will further be understood that depth sensing devices may be used in system 20 that are physically separate from the image sensing portion of video cameras 22. The terms "video camera" or "camera," as used herein, will therefore encompass devices that only detect images, as well as devices that detect both images and depths. The detected images include, in at least some embodiments, both visible light images and thermal images.

In the embodiment shown in FIG. 1, cameras 22 within each room 28 communicate their electronic images to computer device 24 over network 26. If cameras 22 include a depth sensor and/or microphones, the depth sensor signals and/or microphone signals are also forwarded to computer device 24 over network 26. The architecture of FIG. 1 may be modified in a variety of different manners The one or more cameras 22 that are positioned within a given room, or other location, are in electrical communication with a computer device 24 via a communications medium, such as, but not limited to, a hospital network 26, which may be a local area network (network), a wide area network (WAN), or any other type of network, including a network that is coupled to the Internet (FIG. 1). Network 26 may be an Ethernet-based network, or other type of network.

The images recorded by video cameras 22 are converted to electrical signals which are forwarded to computer device 24 for processing in various manners, as will be described in more detail below.

In the embodiment shown in FIG. 1, there are three video cameras 22 positioned within a single room 28. The number of video cameras 22 within a room, or other area, may be varied, and may depend upon what information is gathered from the video images. The physical location of the video cameras 22 within a room or other area may also vary in accordance with the layout of the room—such as, but not limited to, the physical location of the person support apparatus 32 within the room, the location of the restroom, and the location of furniture or objects in the room—such that the cameras 22 are suitably positioned to be able to capture the desired images. As was noted previously, the video cameras 22 may include, in addition to an image sensor, a depth sensor (which may utilize infrared technology), or other sensors. The image sensor may be a digital image sensor in order to facilitate the digital processing of the recorded signals.

Any of the computer devices in communication with network 26, such as EMR device 34, work flow computer device 36, caregiver alerts computer device 38, and the ADT device may comprise one or more conventional servers, PCs, software applications, or other known computing devices. EMR computer device 34 is a conventional computer device of software application adapted to store and process patient electronic medical records. Information gathered from one or more video cameras 22 and processed by computer device 24 is therefore transferable to EMR device 34 such that the processed information is automatically entered into a particular patient's EMR.

Work flow computer device 36 is a conventional computer device or software application adapted to manage the assignment of caregivers to particular patients and to oversee the performance of specific caregiver functions. Information gathered from one or more video cameras 22 and processed by computer device 24 is therefore transferable to work flow computer device 36, thereby avoiding the need for manual entry of such information. Such information includes data identifying the completion, or partial completion, of one or more caregiver tasks and/or the manipulation of one or more virtual control panels on a person support apparatus, such as a bed, stretcher, recliner, cot, operating table, or the like.

Caregiver alerts computer device 38 is also a conventional computer device or software application that is adapted to communicate alerts to caregivers. Computer device 38 may be part of a conventional nurse call computer system, may be completed integrated into such a nurse call computer system, or it may be a stand-alone system separate from the nurse call system. Regardless of its relationship to a nurse call system, caregiver alerts computer device 38 is adapted to forward alerts to caregivers when information about a patient or the support apparatus (e.g. bed, recliner, stretcher, etc.) associated with the patient warrants. Such alerts are forwarded wirelessly to portable communication devices carried by the caregivers (e.g. pagers, personal digital assistants, tablet computers, laptop computers, Blackberries, cell phones, etc.) and/or they are forwarded by wires to nurses stations or audio stations within the vicinity of one or more designated caregivers.

In some embodiments, cameras 22 are mounted to any one or more of the walls, the ceiling, objects within a room, such as the hospital bed or other furniture, or in still other locations. Each camera 22 is either mounted in a fixed orientation, or it is coupled to a mounting structure that allows the orientation of the camera to be automatically adjusted by computer device 24 such that the camera is capable of recording images of different areas of the room by adjusting its orientation. Still further, each camera 22 includes zoom features, in at least one embodiment, that allow computer device 24, or another intelligent device, to control the zooming in and zooming out of the cameras 22 such that both close-up images and wider field of view images may be recorded, as desired.

Each computer device 24 includes software installed thereon that is adapted to process the sensor signals recorded by cameras 22. In one embodiment, such software is conventional software, or includes conventional software components, for recognizing video images and processing the information contained therein. In at least some embodiments, such software combines commercially available software modules with customized software dedicated to carrying out the functions and algorithms described herein. As one example, such commercially available software may include OpenCV, which is an open source computer visions library supported by Willow Garage of Menlo Park, Calif. The OpenCV library has been released under the Berkeley Software Distribution (BSD) open source license. Customized software may be added to interact with, modify, and/or utilize one or more software components of the OpenCV library in order to carry out the algorithms described herein. Other commercially available software may also be used, either in addition to or in lieu of the OpenCV library.

In addition to the components described above, video monitoring system 20 also includes one or more databases 50 (FIG. 1). Each database 50 is constructed to be accessible by computer device 24 such that computer device 24 is able to use the contents of database 50 in carrying out one or more of the algorithms described herein. In one embodiment, such as shown in FIG. 1, database 50 is placed in communication with computer network 26 such that computer device 24 can access the contents of database 50 over network 26. In other embodiments, database 50 is located elsewhere. One or more user input devices 52 are also included in system 20 in order to add, update, or delete information contained with database 50. Such user input devices include keyboards, cameras, scanners, touch screens, bar code readers, or other types of devices.

In at least one embodiment, database 50 contains information regarding different control panel images and their respective controls, including any one or more of the following: data identifying which images to display on different types of person support apparatuses 32; data identifying when the control panel images are to be displayed; data that defines the control panel image; data identifying what things are controlled by the virtual control panel; and data identifying whether the content and/or functionality of the virtual control panel is dependent upon the presence or absence of specific individuals, or specific types of individuals (e.g. caregivers, visitors, technicians, cleaning personnel, administrative personnel, etc.). The information within database 50 also includes data that is specific to individual rooms within the facility, such as features of the room that are potentially controllable via a virtual control panel, such as, but not limited to, a television, a thermostat, a movable curtain, a telephone, and other device.

Figure 2:
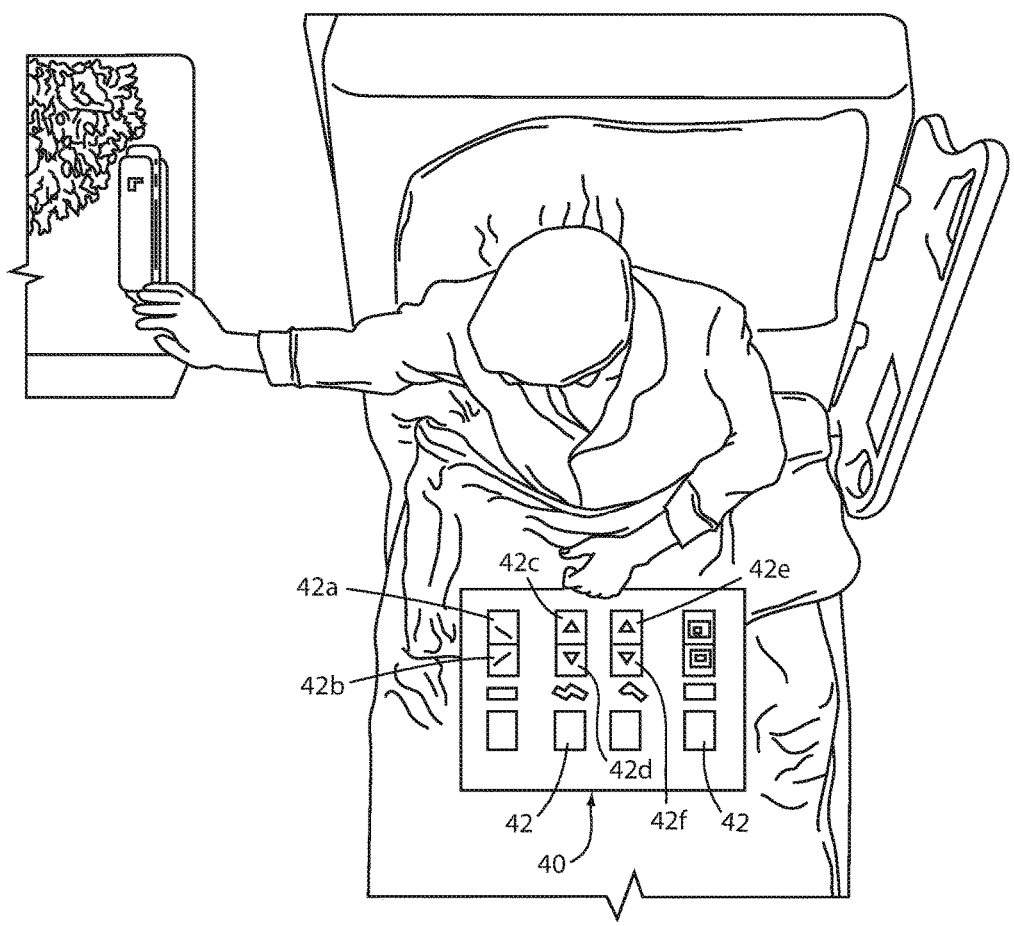
FIG. 2 is a perspective view of an example of a projected image of a virtual control panel projected onto an area of a bed by any one of the video monitoring systems of FIG. 1, 3 or 4.

FIG. 2 illustrates an example of a user interface image or control panel image 40 that is projected by image projector 30 onto a person support apparatus 32. Control panel image 40 includes multiple button images 42 that are displayed by projector 30 in front of a patient sitting in person support apparatus 32. The movement of the patient's hand or finger onto the surface on which a selected one of these button images 42 is displayed is interpreted as the patient desiring to press a real button corresponding to that button's image. System 20 then acts accordingly to cause the proper response. Images of such user interfaces may be projected for controlling the environment of the room (lights, TV, sound, radio, etc.), adjustments to the bed, and/or for communicating with a nurse. System 20 is configured, in at least one embodiment, to be in electrical communication with all of these devices such that, when a patient moves in a manner indicating a selection of a particular function (based on choosing control from a projected images of controls), system 20 causes the device to react in the manner desired by the patient.

In the embodiment shown in FIG. 2, control panel image 40 includes a plurality of control images 42 for controlling different aspects of person support apparatus 32. More specifically, control panel image 40 includes tilting control images 42a and 42b, leg section pivoting control images 42c and 42d, head section pivoting control images 42e and 42f, as well as still other control images 42. When the patient moves his or her arm and presses down on control panel image 40 at the location of any of control images 42, one or more cameras 22 capture this movement and forward the captured images to computer device 24 which interprets the images as indicating that the patient desires to active the actual control corresponding the particular control image that has been touched by the patient. Computer device 24 then sends a control signal to the corresponding actuator or device that carries out the desired command.

Thus, when a patient presses down on tilt control image 42a, computer device 24 sends a message to person support apparatus 32 instructing it to tilt the entire support deck of person support apparatus 32 in a first direction. When the patient presses down on tilt control image 42b, computer device 24 sends a message to person support apparatus 32 instructing it to tilt the entire support deck of the person support apparatus 32 in a second direction that is opposite to the first direction. When the patient presses down on pivot control images 42c and 42d, computer device 24 sends a message to person support apparatus 32 instructing it to pivot a leg or knee section of the support deck of the person support apparatus 32 up and down, respectively. When the patient presses down on pivot control images 42e and 42f, computer device 24 sends a message to person support apparatus 32 instructing it to pivot a head section of the support deck of the person support apparatus 32 up and down, respectively. Other aspects of person support apparatus 32 are also controllable via one or more of the other control images 42 shown in the control panel image 40 of FIG. 2.

Although FIG. 2 illustrates a control panel image 40 that is projected onto the bedding of person support apparatus 32 and that includes control images 42 that are intended to be activated by a patient of person support apparatus 32, it will be understood that video monitoring system 20 is adapted in other embodiments to project control panel images 40 onto other locations of person support apparatus 32, as well as to project control panel images 40 that includes control images intended to be activated by persons other than patients. For example, in one embodiment, video monitoring system 20 projects a control panel image 40 onto a footboard of person support apparatus 32 that includes control images 42 that are intended to be activated or deactivated by a caregiver. In still another embodiment, video monitoring system 20 projects a control panel image 40 onto one or both sides of a siderail of person support apparatus 32. One of such control panel images 40 may be intended for the patient and the other intended for a caregiver, or they may be intended for other personnel.

In some embodiments of video monitoring system, computer device 24 is further adapted to change the one or more control panel images 40 that are projected by one or more projectors 30 in response to the presence or absence of certain individuals and/or classes of individuals. For example, in one embodiment, video monitoring system 20 processes the images from cameras 22 in order to detect when a clinician enters a room. System 20 determines the identity of the specific caregiver by means of facial recognition software, a badge identification process based upon a specific badge that the caregiver is carrying, by software that recognizes the attire worn by the caregiver, or by a combination of one or more of these means, or by still other means.

In response to detecting the presence of a caregiver in a specific room 28, or within the vicinity of a specific person support apparatus 32, computer device 24 is adapted to change the control panel image 40 that is projected by projector 30 in one or more manners. In one embodiment, computer device 24 stops projecting control panel image 40 intended for use by caregivers whenever caregivers exit room 28, or otherwise leave the vicinity of person support apparatus 32. When the caregiver returns, video monitoring system 20 re-projects the control panel image 40 so that the caregiver can use the controls that are controlled by the control panel image.

In addition to, or in lieu of, turning on and off the projection of control panel image 40 in response to the presence or absence of a caregiver, video monitoring system 20 is also adapted in at least one embodiment to change the content of control panel image 40 in response to the presence or absence of a caregiver. Thus, for example, when a caregiver approaches person support apparatus 32, system 20 is configured in one embodiment to change the content of control panel image 40 to include additional control images 42. The additional control images 42 are for items that are intended to only be controlled by a caregiver, rather than a patient, or other person. One example of such a control image 42 that is added in the presence of a caregiver to image 40 and deleted in the absence of the caregiver is a control image 42 that arms and disarms a bed exit alert system on board person support apparatus 32. Some examples of such alert systems are disclosed in commonly assigned U.S. Pat. No. 5,276,432 issued to Travis and entitled PATIENT EXIT DETECTION MECHANISM FOR HOSPITAL BED; commonly assigned U.S. patent application Ser. No. 14/212,367 filed Mar. 14, 2014 by inventors Michael Joseph Hayes et al. and entitled PATIENT SUPPORT APPARATUS WITH PATIENT INFORMATION SENSORS; and commonly assigned U.S. patent application Ser. No. 62/065,242, filed Oct. 17, 2014 by inventors Marko Kostic et al. and entitled PERSON SUPPORT APPARATUSES WITH MOTION MONITORING; and commonly assigned U.S. patent application Ser. No. 61/989,243 filed May 6, 2014 by inventors Marko Kostic et al. and entitled PERSON SUPPORT APPARATUS WITH POSITION MONITORING, the complete disclosures of all of which are incorporated herein by reference. Other types of bed exit systems may also be used with person support apparatus 32.

Other types of control images that are selectively projected by projector 30 in the presence of authorized caregivers and not displayed in the absence of authorized caregivers include one or more lockout control images 42. Such lockout control images, when activated, lock out certain motions of person support apparatus 32 such that an occupant of person support apparatus 32 cannot move person support apparatus in the locked out manners, even if the occupant attempts to move person support apparatus via an actual control that is part of an actual separate control panel (i.e. not an image of a control panel). Still other types of control images that are selectively projected by projector 30 based on the absence/presence of a caregiver within the vicinity of person support apparatus 32 include any one or more of the following: one or more control images 42 for taking an occupant's weight reading; one or more control images for activating/deactivating a brake on person support apparatus 32; and any one or more control images for activating/deactivating alarms associated with the status of one or more components of person support apparatus 32.

It will be understood by those skilled in the art that computer device 24 is configured in such a manner that when projector 30 ceases to display one or more control images 42, computer device 24 will disable the associated features that are otherwise controlled by those control images 42. Thus, for example, if projector 30 stops projecting a control image 42 for a brake onto a specific surface on person support apparatus 32, a user who presses his or her finger or hand on that specific surface will not activate or deactivate the brake of the person support apparatus. In other words, when computer device 24 instructs projector 30 to stop displaying a control image 42, it also stops reacting to any images from cameras 22 that indicate a user pressing his or her fingers or hand against the surface that the control image was projected onto.

Control panel image 40 also includes, in at least some embodiments, one or more control images 42 that are used by caregivers to indicate when specific tasks have been completed by the caregiver. For example, one or more control images 42 are included on a control panel image 40, in at least one embodiment, that are activated by a caregiver when the caregiver completes any one or more of the following tasks: turns a patient, checks one or more of the patient's vital signs, completes a patient rounding task, weighs a patient, or performs any other patient care task. In such cases, the activation of the corresponding control image 42 is forwarded by computer device 24 to either or both of EMR computer device 34 and/or work flow computer device 36 in order to update the records maintained thereon.

Figure 3:
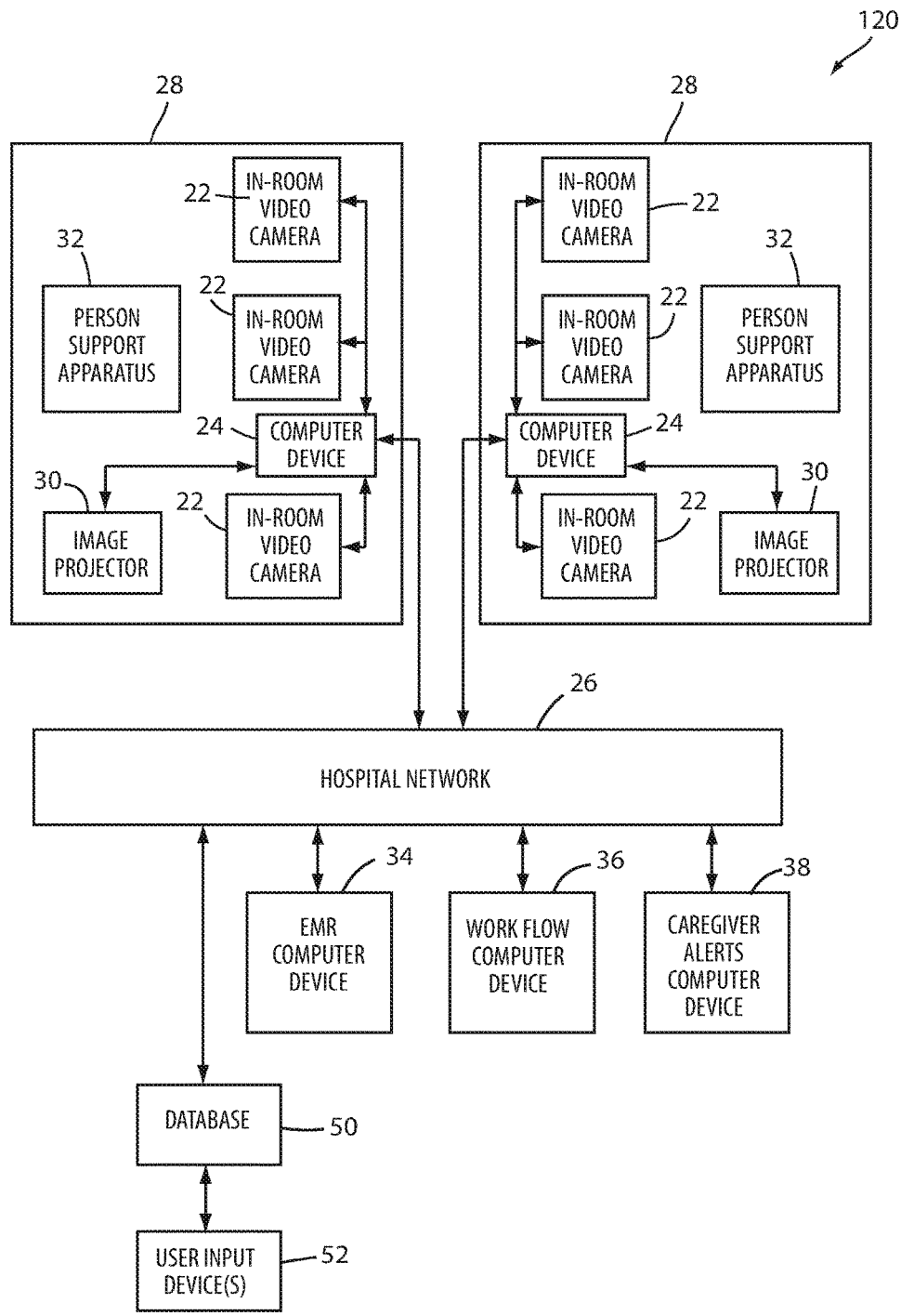
FIG. 3 is a block diagram of a video monitoring system according to a second embodiment.

FIG. 3 illustrates a video monitoring system 120 according to another embodiment. Those components of video monitoring system 120 that are the same as, and that operate in the same manner as, the components of video monitoring system 20 are labeled with the same reference numbers. Because these components are the same as, and operate in the same manner as, those that have been previously described, they are not described again below.

Video monitoring system 120 differs from video monitoring system 20 in that one or more computer devices 24 are positioned within rooms 28. Each computer device 24 processes the images obtained from one or more video cameras 22 that are positioned in the same room as computer device 24. In at least one version of video monitoring system, each computer device 24 is in communication with hospital network 26 and those computer devices that are part of the network 26 (e.g. EMR computer device 34, work flow computer device 36, etc.). Computer device 24 carries out the same processing and communication features as discussed previously. In at least one embodiment, computer device 24 receives data defining one or more control panel images 40 and their associated control images 42 from database 50. Computer device 24 then displays the one or more control panel images 40 and their associated control images 42 in one or more selected locations within room 28. Cameras 22 capture images of the control panel image which are processed by computer device 24 to determine if a user has activated any of the control images 42 within the control panel image 40. If so, computer device 24 forwards a message or command to the device or devices (e.g. person support apparatus 32) that corresponds to the functions controlled by the control image 42, as described above.

Figure 4:
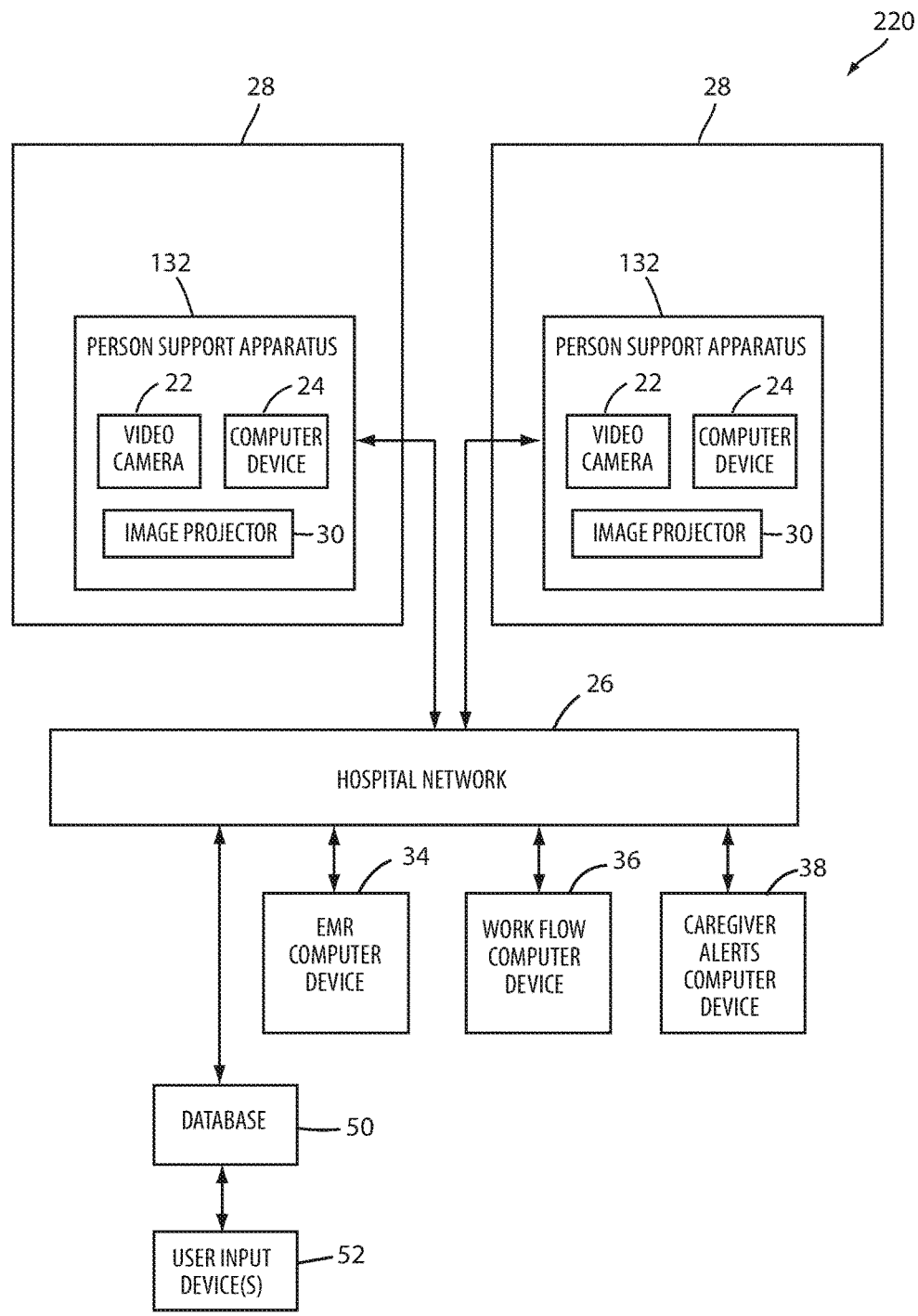
FIG. 4 is a block diagram of a video monitoring system according to a third embodiment.

FIG. 4 illustrates a video monitoring system 220 according to another embodiment. Those components of video monitoring system 220 that are the same as, and that operate in the same manner as, the components of video monitoring system 20 are labeled with the same reference numbers. Because these components are the same as, and operate in the same manner as, those that have been previously described, they are not described again below.

Video monitoring system 220 differs from video monitoring systems 20 and/or 120 in that computer device 24, projector 30, and at least one camera 22 are all incorporated into a person support apparatus 132. Projector 30 is adapted to display one or more control panel images 40 on one or more surfaces of person support apparatus 132. The displayed control panel images 40 are monitored by one or more cameras 22, each of which is in communication with computer device 24. Computer device 24 processes the images obtained from one or more video cameras 22 and carries out the corresponding actions based upon a user's contact with the one or more control images 42 in the control panel image 40. Computer device 24 in person support apparatus 132 is, in one embodiment, also responsible for controlling the functions of person support apparatus 132, such as, but not limited to, raising, lowering, and/or pivoting sections of the support apparatus, activating an exit alert system, etc. In other embodiments, computer device 24 is in communication with a separate controller that oversees and controls the movements, and other functions, of person support apparatus 132. In any of the person support apparatuses 132 of system 220, multiple image projectors 30 and video cameras 22 may be included in order to project and monitor multiple control panel images 40 at different locations on person support apparatus 132, thereby creating more than one virtual control panel on the person support apparatus 132.

In any of the video monitoring systems 20, 120, and/or 220 described above, each video camera 22 can be modified to include its own computer device 24 or its own portion of computer device 24, either separately attached thereto, or integrated into the camera 22 itself. In such embodiments, each computer device 24 is dedicated to processing, or pre-processing, the electronic images, depth sensor readings, and/or voice signals gathered by the associated video camera 22. The results of such processing, or pre-processing, are then forwarded directly to network 26, or to one or more intermediate computers (not shown) before being sent to network 26. Computer devices 24 provide the software intelligence for processing the images, depth sensor data, and/or voice data recorded by cameras 22, and the precise physical location of this intelligence can vary in a wide variety of different manners, from embodiments in which all the intelligence is centrally located to other embodiments wherein multiple computing structures are included and the intelligence is physically distributed throughout the care giving facility.

In any of the video monitoring systems 20, 120, and 220 described above, as well as any of their variations, it will be understood that the system can further be modified to include any one or more of the additional features disclosed in the two commonly assigned U.S. patent applications to which the present application claims priority and incorporates by reference; namely, U.S. patent application Ser. No. 13/242,022 filed Sep. 23, 2011 by inventors Richard A. Derenne et al. and entitled VIDEO MONITORING SYSTEM and U.S. provisional patent application Ser. No. 61/385,607 filed Sep. 23, 2010, by inventors Richard A. Derenne et al. and entitled VIDEO MONITORING SYSTEM.

Figure 5:
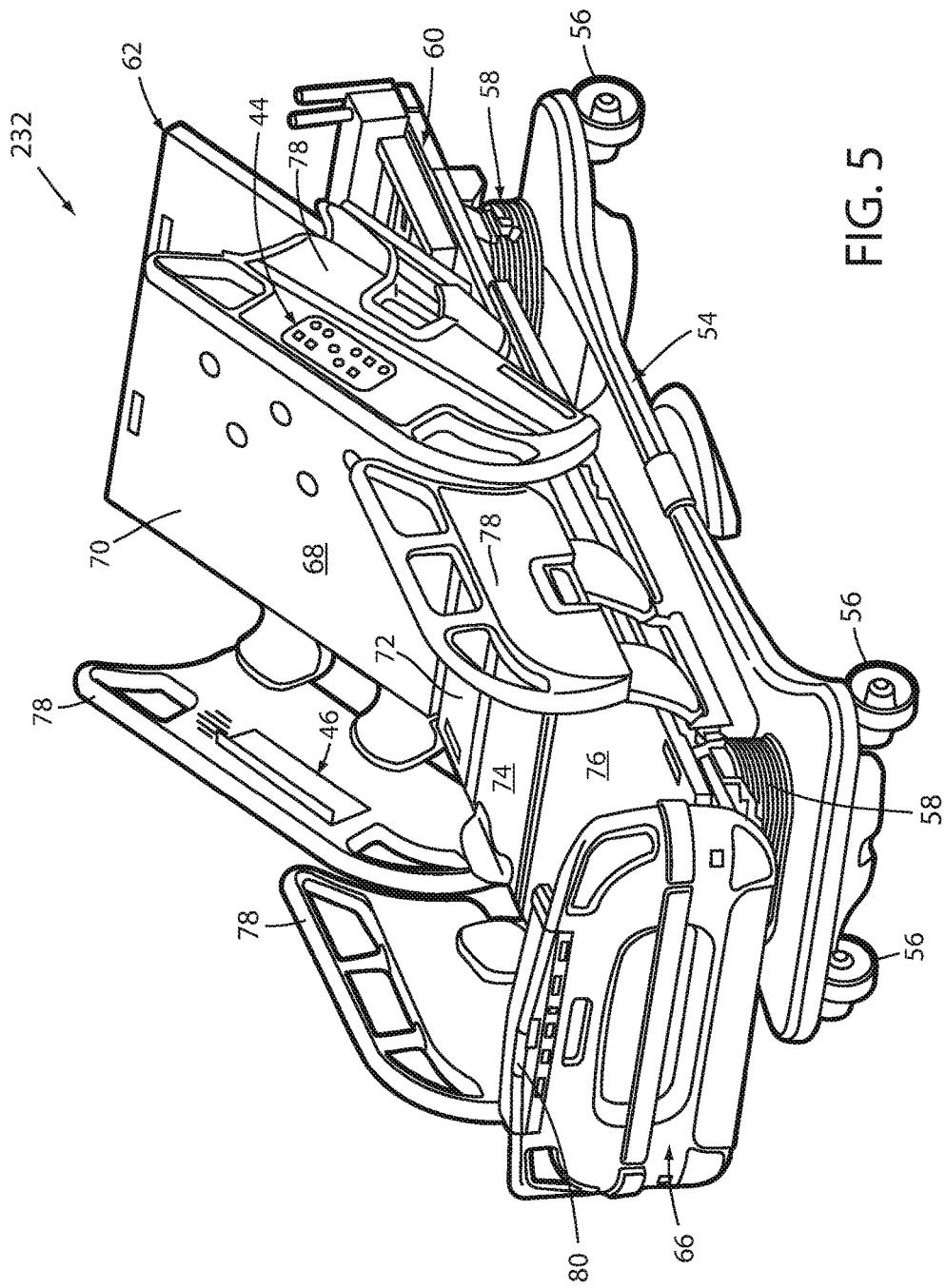
FIG. 5 is a perspective view of a person support apparatus according to another embodiment of the invention.

A person support apparatus 232 according to another embodiment of the invention is shown in FIG. 5. Person support apparatus 232 includes at least one virtual control panel 46 in addition to a conventional or actual control panel 44. Although person support apparatus 232 is shown as a bed adapted for use in a hospital or other medical setting, it will be understood that person support apparatus 232 could be, in different embodiments, a cot, a stretcher, a gurney, a recliner, an operating table, a residential bed, or any other structure capable of supporting a person, whether stationary or mobile and/or whether medical or residential.

In general, person support apparatus 232 includes a base 54 having a plurality of wheels 56, elevation adjustment mechanisms 58 supported on the base, a frame 60 supported on the elevation adjustment mechanisms, and a support deck 62 supported on the frame. Person support apparatus 232 further includes a footboard 66.

Base 54 includes a brake that is adapted to selectively lock and unlock wheels 56 so that, when unlocked, person support apparatus 232 may be wheeled to different locations. Elevation adjustment mechanisms 58 are adapted to raise and lower frame 60 with respect to base 54. Elevation adjustment mechanisms 58 may be hydraulic actuators, electric actuators, or any other suitable device for raising and lowering frame 60 with respect to base 54. In some embodiments, elevation adjustment mechanisms 58 are operable independently so that the orientation of frame 60 with respect to base 54 can also be adjusted.

Frame 60 provides a structure for supporting support deck 62 and footboard 66. Support deck 62 provides a support surface 68 on which a mattress (not shown), or other cushion is positionable so that a person may lie and/or sit thereon. Support deck 62 is made of a plurality of sections, some of which are pivotable about generally horizontal pivot axes. In the embodiment shown in FIG. 1, person support deck 62 includes a head section 70, a seat section 72, a thigh section 74, and a foot section 76. Head section 70, which is also sometimes referred to as a Fowler section, is pivotable about a generally horizontal pivot axis between a generally horizontal orientation (not shown in FIG. 5) and a plurality of raised positions (one of which is shown in FIG. 5). Thigh section 74 and foot section 76 may also be pivotable.

A plurality of side rails 78 (FIG. 5) may also be coupled to frame 60. If person support apparatus 232 is a bed, there may be four such siderails, one positioned at a left head end of frame 60, a second positioned at a left foot end of frame 60, a third positioned at a right head end of frame 60, and a fourth positioned at a right foot end of frame 60. If person support apparatus 232 is a stretcher or a cot, there may be fewer siderails. In other embodiments, there may be no siderails on person support apparatus 232. Regardless of the number of siderails, such siderails are movable between a raised position in which they block ingress and egress into and out of person support apparatus 232, and a lowered position in which they are not an obstacle to such ingress and egress.

The construction of any of base 54, elevation adjustment mechanisms 58, frame 60, support deck 62, footboard 66, and/or side rails 78 may take on any known or conventional design, such as, for example, that disclosed in commonly assigned, U.S. Pat. No. 7,690,059 issued to Lemire et al., and entitled HOSPITAL BED, the complete disclosure of which is incorporated herein by reference; or that disclosed in commonly assigned U.S. Pat. publication No. 23207/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The construction of any of base 54, elevation adjustment mechanisms 58, frame 60, support deck 62, footboard 66 and/or the side rails may also take on forms different from what is disclosed in the aforementioned patent and patent publication.

In the embodiment shown in FIG. 5, person support apparatus 232 includes two actual control panels 44 (only one visible in FIG. 5) that are positioned on the outside faces of the head end side rails 78. Actual control panels 44 may take on any conventional form, such as, but not limited to, control panels that include a plurality of buttons, switches, touchscreens, or the like. Person support apparatus 232 also includes two virtual control panels 46 (only one visible in FIG. 5) that are positioned on the inside faces of the head end side rails 78. Person support apparatus 232 further includes an additional footboard control panel (not labeled in FIG. 5) that is positioned underneath a pivotable cover 80. In some embodiments, this footboard control panel is a virtual control panel 46, while in other embodiments it is an actual control panel 44.

It will be understood by those skilled in the art that the particular number and arrangement of virtual control panels 46 on person support apparatus 232 can be modified from that shown in FIG. 5. For example, person support apparatus 232, in at least one embodiment, has all of its control panels implemented as virtual control panels 46. In another embodiment, the control panels on the side rails are all implemented as physical control panels 44 while the footboard control panel is implemented as a virtual control panel 46. Other arrangements are also possible.

Figure 6:
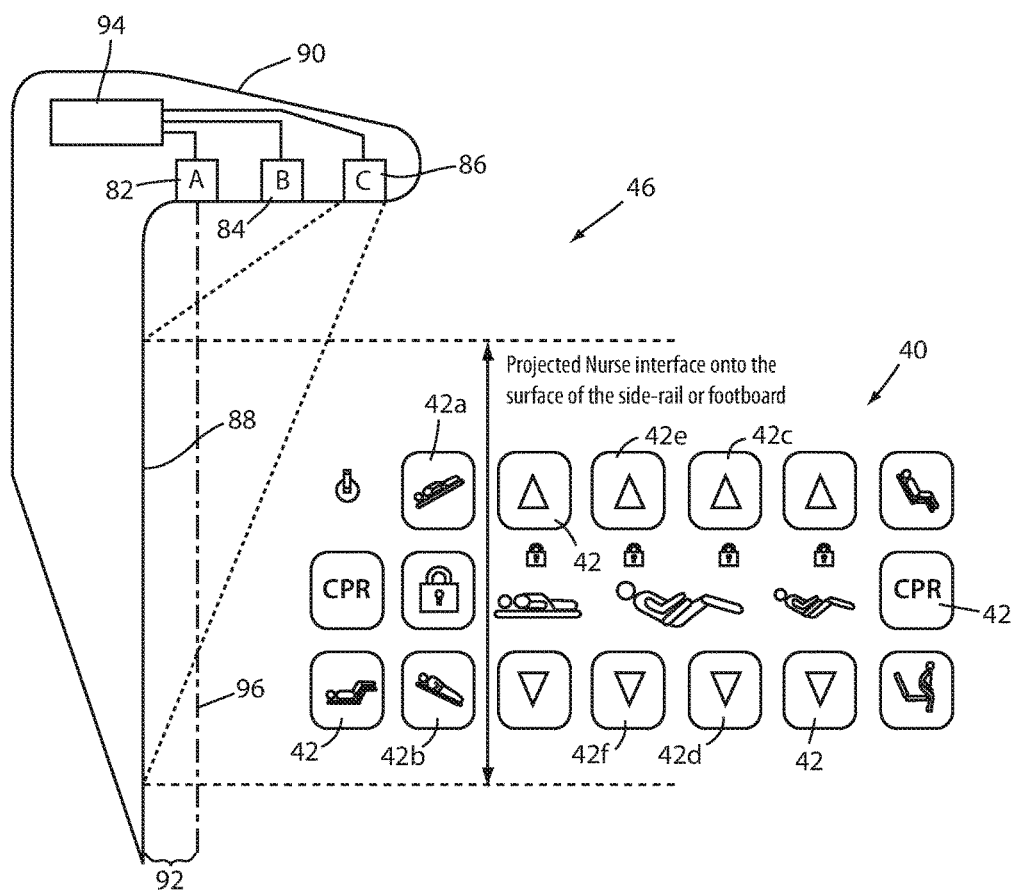
FIG. 6 is a side, elevation view of components of a virtual control panel that is adapted to be incorporated into a person support apparatus, such as, but not limited to, the person support apparatus of FIG. 5.

FIG. 6 illustrates in greater detail one manner in which virtual control panels 46 are constructed. Virtual control panel 46 includes an infrared laser diode 82, an image sensor 84, a controller 94, a laser diode 86, and a diffractive optical element (not shown) that is positioned adjacent laser diode 86. Laser diode 86 and the diffractive element function in the same manner as projector 30. That is, laser diode 86 and its associated diffractive element project a control panel image 40 onto a generally flat surface 88 of person support apparatus 232. Infrared laser diode 82, image sensor 84, and laser diode 86 are all physically coupled to an overhang 90 that is positioned above the surface 88.

Controller 94 is in communication with infrared laser diode 82, image sensor 84, and laser diode 86. Although controller 94 is shown in FIG. 6 physically located within overhang 90, it will be understood that this is done merely for purposes of illustration and that the physical location of controller 94 can be at any suitable location on person support apparatus 232, or, in some embodiments, remote from person support apparatus 232. In at least several embodiments, controller 94 is programmed to carry out the same functions as computer device 24 described above. Controller 94 is an electronic structure configured to carry out the logic and algorithms described herein and includes any combination of one or more processors, systems on chip (SoC), field programmable gate arrays (FPGA), microcontrollers, discrete logic circuitry, software and/or firmware. Regardless of whether controller 94 is a single physical device, or is multiple physical devices working together (which may be located in different physical locations), controller 94 represents the hardware, software and/or firmware necessary to carry out the algorithms described herein.

As noted, laser diode 86 and its associated diffractive optical element project a control panel image 40 onto surface 88. One example of such a projected control panel image 40 is shown in FIG. 6. It will be understood by those skilled in the art that the control panel image 40 of FIG. 6 is merely one illustrative example of many different variations of control panel images 40 that can be projected by laser diode 86. The control panel image 40 that is projected by laser diode 86 is etched into a lens of the laser diode 86 in one embodiment. The diffractive element of laser diode 86 diffracts this image so that it is properly displayed on surface 88. The etching may take place using any conventional process, as would be known to one of ordinary skill in the art.

Image sensor 84 senses whether a user has moved his or her hand or finger within a threshold distance 92 of surface 88. Image sensor 84 accomplishes this using any known manner, as would be known to one skilled in the art. In at least one embodiment, image sensor 84 and/or controller 94 analyze the detected images and calculate a centroid of the finger, arm, or other object that has entered the field of view of image sensor 84 (and penetrated past threshold distance 92, as discussed below). Image sensor 84 is, in one embodiment, a CMOS based image sensor. In other embodiments, image sensor 84 is a Charge Coupled Device (CCD) image sensor. In still other embodiments, other types of imaging sensing technologies are used.

When image sensor 84 detects that the user's hand or finger has moved within threshold distance 92 of surface 88, controller 94 determines the location on surface 88 at which the user's hand or finger moved within threshold distance 92. After determining this location, controller 94 determines which one (if any) of the various control images 42 is displayed at that location on surface 88. Controller 94 then either carries out the action itself that corresponds to that control image 42, or it forwards a message to the appropriate device, structure, or other component that carries out the action corresponding to the selected control image 42.

Controller 94 determines whether a user's hands or fingers have moved within threshold distance 92 of surface 88 by way of a plane of infrared light 96 that is emitted from infrared laser diode 82. When the user's hands or fingers penetrate this plane, they scatter the infrared light emitted from laser diode 82. This scattered light is also detected by image sensor 84 and its detection is interpreted by controller 94 as an indication that infrared light plane 96 has been penetrated.

The actual value of threshold distance 92 can vary from embodiment to embodiment. In some embodiments, threshold distance 92 is on the order of a couple of millimeters. In other embodiments, threshold distance is substantially zero. In still other embodiments, larger threshold distances 92 are used. In the embodiment illustrated in FIG. 6, the plane of infrared light 96 is emitted generally parallel to surface 88. It will be understood that, in other embodiments, surface 88 is non-flat, or plane of light 96 is oriented at an angle with respect to surface 88 such that threshold distance 92 is not constant for the entire area of surface 88 on which control panel image 40 is projected.

So long as the actual value of threshold distance 92 is non-zero, it is not necessary for a user to actually make physical contact with surface 88 in order to activate one of the features of the control panel image 40. That is, virtual control panel 46 will activate the corresponding function or feature whenever the user's hand or finger penetrates the plane of light 96. Control of person support apparatus 232 can therefore be carried out without requiring a user to make physical contact with surface 88. This can be advantageous for reducing the possibility of transferring infectious agents between the user and person support apparatus 232. Alternatively, and/or additionally, because surface 88 is generally flat and does not include corners, discontinuities, or other difficult-to-clean spaces, it is easily sanitized, thereby also reducing the possibility of transferring infectious agents.

In still other embodiments, virtual control panel 46 includes a second light projector (not shown) that is positioned an even larger threshold distance away from surface 88 than infrared laser diode 82 (i.e. a distance greater than threshold distance 92). The second light projector projects a plane of light that, when crossed, activates laser diode 86, thereby projecting control panel image 40 onto surface 88. In these embodiments, a user does not see any control image on surface 88 until he or she moves his or her hand or finger sufficiently close to surface 88 to penetrate the second plane of light created by the second light projector. Control panel image 40 therefore only appears to a user when he or she moves his or her hands within a predefined vicinity of surface 88. After moving his or her hand or fingers within this vicinity, controller 94 controls laser diode 86 such that control panel image 40 remains illuminated for a predetermined amount of time thereafter, or until the second plane of light is broken once again. The braking of this second plane of light is detected by image sensor 84, in one embodiment. In other embodiments, a separate sensor is used for detecting the crossing of this second plane of light. The separate sensor is in communication with controller 94.

Although virtual control panel 46 has been described herein as utilizing an infrared laser diode 82 for creating plane of light 96, it will be understood by those skilled in the art that light having frequencies outside of the infrared spectrum can be used for detecting the presence of a caregiver's fingers, arm, or other object within threshold distance 92. Thus, infrared laser diode 82 is replaced with a light emitter that emits light of a non-IR frequency in at least one embodiment. It will also be understood that, regardless of whether or not infrared light is used or not, the detection of when a user breaks light plane 96 can be modified from that shown in FIG. 6. More specifically, one or more dedicated sensors are placed in line with light plane 96 and on a side of image 40 opposite the light emitter (e.g. diode 82). Such detectors detect an interruption in the emitted light and forward a message indicative of the interruption to controller 94. Other variations are also possible.

In still other embodiments, laser diode 86 is replaced with a Liquid Crystal Display (LCD) projector and/or a holographic image projector. When so equipped, control panel image 40 can be rendered dynamic. That is, the specific control panel image 40 displayed by the LCD or holographic projector can be changed in different contexts. More specifically, by using an LCD projector or holographic projector instead of laser diode 86, control panel image 40 can be changed in any of the ways previously described above with respect to projector 30. Thus, for example, control panel image 40 can be changed based upon the presence or absence of certain individuals or classes of individuals, the state of person support apparatus 232, etc.

Although control panel image 40 shown in FIG. 6 includes a specific set of control images 42, it will be understood by those skilled in the art that any of the functions previously described above with respect to video monitoring systems 20, 120, and/or 220 can be carried out using virtual control panel 46. Thus, control panel image 40 can be modified to include any one or more control images 42 for carrying out any of the functions previously described above.

In at least one embodiment, person support apparatus 232 is further modified to include an ambient light sensor (not shown) that is positioned within the vicinity of surface 88. The ambient light sensor communicates ambient light readings to controller 94. Controller 94 adjusts the intensity at which laser diode 86 (or the LCD projector or holographic projector) projects control panel image 40 onto surface 88. That is, controller 94 increases the intensity at which image 40 is projected when ambient light levels are higher and decreases the intensity when ambient light levels are lower. If person support apparatus 232 includes multiple virtual control panels 46, each one may include its own ambient light sensor.

In at least one other embodiment, virtual control panel 46 is modified by eliminating laser diode 86 and the control panel image 40 projected thereby. Instead of projecting an image of a control panel onto surface 88, a picture of the image is printed, or otherwise integrated into, surface 88. In one embodiment, the picture is part of a sticker that is adhesively secured to surface 88. In another embodiment, the picture is painted, etched, printed, or otherwise, secured to surface 88. Regardless of the manner in which the picture is secured to surface 88, the picture includes one or more controls, such as those found in the control panel image 40. In at least one embodiment, the picture is flat so that it can easily be cleaned and disinfected. It may include a protective covering that seals it against damage from the chemicals used to disinfect it. Image sensor 84 and laser diode 82 operate with respect to the picture in the same manner described above; namely, they detect when a user moves his or her finger and/or arm within threshold distance 92 of the picture. When this happens, controller 94 activates the feature that corresponds to the control that was "pressed" in the picture, just as is done when the user moves his or her finger/arm within the threshold distance of control panel image 40.

In still other embodiments, virtual control panel 46 is in communication with computer network 26 and/or any of the computer devices (e.g. computer devices 34, 36, 38, etc.) that are coupled to computer network 26. Virtual control panel 46 thereby allows a user to use virtual control panel 46 to control one or more features of these computer devices, including any of the features described above with respect to video monitoring systems 20, 120, and/or 220.

In still another embodiment, person support apparatus 232 is adapted for use in a medical setting and includes at least one patient virtual control panel 46 and at least one caregiver control panel that may be physical or virtual. The patient virtual control panel 46 includes at least one control image for controlling the movement of one or more components of the person support apparatus. As one example, the patient virtual control panel 46 includes control images for controlling a height of support surface 68 and/or the pivoting of a section of the support surface 68. The caregiver control panel includes at least one control for locking the one or move movement controls of the patient's virtual control panel. That is, the caregiver control panel includes at least one control that renders those control images of the patient's virtual control panel corresponding to movement of the person support apparatus inoperative. The caregiver control panel is in communication with the patient virtual control panel and causes the locked out control images to not be projected when they are locked out. In this manner, when the patient controls are locked out, the patient does not still see a control image of the function that has been rendered inoperative (i.e. locked out). This avoids the potential frustration that a patient might otherwise experience by attempting to manipulate a visible control that might have been rendered inoperative without their knowledge. When the caregiver ceases the lock out feature (i.e. renders the patient's virtual control panel operative again), the caregiver control panel communicates a signal to the virtual control panel instructing the virtual control panel to once again display the control image corresponding to the previously locked out feature.

In still another embodiment, person support apparatus 232 is adapted to communicate with one or more separate devices and to allow the separate device to utilize all or a portion of surface 88 for projecting one or more control images associated with the control of that device. In one embodiment, a DVT pump for treating a patient supported by person support apparatus 232 is provided and the DVT pump includes a cable that plugs into a port on person support apparatus 232 that is in communication with controller 94. The DVT pump sends data to controller 94 that defines a control panel image 40, or a portion of a control panel image 40, that includes control images 42 for controlling one or more aspects of the DVT pump. Controller 94 displays this image on surface 88, either in lieu of, or in addition to, the control panel image 40 that it displays for controlling person support apparatus 232. When a user moves his or her finger past threshold distance 92 for one of the corresponding control images 42 on the control panel image 40, this is detected by image sensor 84 and processed by controller 94. Controller 94 then sends a message to the DVT pump indicating which control image 42 was activated and the internal circuitry within the DVT pump reacts accordingly. Person support apparatus 232 therefore provides a virtual control panel 46 that can be switched from controlling person support apparatus 232 to one or more ancillary devices.

Other ancillary devices that can be controlled by virtual control panel 46 besides a DVT pump include monitors, thermal regulation devices, compression boots, mattresses, physiological sensors, etc. Such ancillary devices include data defining one or more control panel images that are forwarded—either via a wire or wirelessly—to the person support apparatus. The data includes information identifying the various control images and their respective locations on the control panel image. The person support apparatus receives this information and projects the control panel image onto one or more surfaces on the person support apparatus. The image sensor monitors the control images and detects the presence of a user's finger. When a user's finger is detected, image sensor 84 reports this to the ancillary device, along with the specific control image that the user's finger has pressed (or moved within the threshold distance). The ancillary device then reacts accordingly. By allowing ancillary devices to project control panel images on the person support apparatus, the person support apparatus does not need hard coding that is specifically tailored to each ancillary device in order to allow control to be carried out using a control panel on the person support apparatus. Instead, the person support apparatus can, in effect, lease its virtual control panel 46 to the ancillary device without knowing any details about the ancillary device or its operation.

When virtual control panel 46 is used to control an ancillary device, person support apparatus 232 retains, in at least one embodiment, some portion of the virtual control panel image space in which a control image switch is displayed. The control image switch, when activated, switches the content of the virtual control panel back and forth between a control panel image that controls person support apparatus 232 and a control panel image that controls the ancillary device. The image control switch always remains visible and active so that a user can toggle back and forth between controlling person support apparatus 232 and the ancillary device.

In still other embodiments, the content of the control panel image 40, as well as the functions controlled thereby, are communicated to the person support apparatus 232 from computer network 26 and configured to control one or more of the client software applications, or person support apparatus apps that are disclosed in commonly assigned U.S. patent application Ser. No. 14/211,613 filed Mar. 14, 2014, by inventors Michael Joseph Hayes et al. and entitled PATIENT SUPPORT APPARATUS WITH REMOTE COMMUNICATIONS, the complete disclosure of which is hereby incorporated herein by reference. Virtual control panel 46 is thus specifically tailored, in at least some embodiments, to control one or more services, treatments, and/or other features that are specific to the individual (e.g. patient) occupying person support apparatus 232.

One or more virtual control panels 46 can also be included on person support apparatus that change the content of their control panel images 40 in response to any of the software apps, applications, and/or features that are added to, or selectively enabled on, a person support apparatus 232 after initial purchase, such as disclosed in commonly assigned U.S. patent application Ser. No. 62/081,744 filed Nov. 19, 2014, by inventors Daniel V. Brosnan et al. and entitled MEDICAL APPARATUS WITH SELECTIVELY ENABLED FEATURES, the complete disclosure of which is also hereby incorporated herein by reference.

Various additional alterations and changes beyond those already mentioned herein can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A person support apparatus comprising: a frame; a support adapted to support a person thereon; an actuator adapted to move a component of the person support apparatus when actuated; an external surface defined on a component of the person support apparatus; a control panel including a lockout control for locking out movement of the actuator; an image projector positioned externally of the component and adapted to project a first control image or a second control image onto the external surface such that a reflection of the first or second control image from the external surface is visible to a user positioned externally of the component, the first control image including an actuator control image for controlling movement of the actuator and the second control image not including the actuator control image, the image projector further adapted to project the first control image only when the lockout control is not activated and to project the second control image when the lockout control is activated; an image sensor positioned externally of the component and adapted to capture images of a user's finger when positioned near the external surface; and a controller adapted to analyze images from the image sensor and determine if the user has moved a finger within a threshold distance of a location on the external surface at which the actuator control image is located and, if so, the controller is adapted to actuate the actuator when the first control image is projected but not when the second control image is projected.

2. The person support apparatus of claim 1 wherein the threshold distance is zero and the controller is adapted to determine if the user has touched the location on the external surface at which the actuator control image is located before actuating the actuator.

3. The person support apparatus of claim 1 wherein the image sensor comprises both an optical camera and an infrared detector, the infrared detector adapted to determine if the user's finger has moved within the threshold distance of the location on the external surface at which the actuator control image is located.

4. The person support apparatus of claim 3 further comprising an infrared light source adapted to project a beam of infrared light along a plane that is generally parallel to the external surface and spaced from the external surface the threshold distance, the infrared detector adapted to detect reflections of the infrared light when the user's finger intersects the infrared light.

5. The person support apparatus of claim 1 wherein the person support apparatus is a bed having a footboard and the image projector and image sensor are both positioned at the footboard.

6. The person support apparatus of claim 1 wherein the person support apparatus is a bed having a plurality of siderails and the image projector and image sensor are both positioned at one of the siderails.

7. The person support apparatus of claim 1 further comprising a second image projector, the second image projector adapted to project a third or fourth control image onto the external surface that is superimposed on the first or second control image, respectively, the third control image including the actuator control image and the fourth control image not including the actuator control image.

8. The person support apparatus of claim 1 wherein the controller is adapted to actuate the actuator for as long as the user's finger remains within the threshold distance of the location on the external surface at which the actuator control image is located, and to de-actuate the actuator when the user's finger moves outside of the threshold distance of the location on the external surface at which the actuator control image is located.

9. The person support apparatus of claim 1 wherein the actuator is adapted to change a height of the support when actuated.

10. The person support apparatus of claim 1 wherein the threshold distance is greater than two millimeters.

11. The person support apparatus of claim 1 further comprising:
a port adapted to communicatively couple to an ancillary device separate from the person support apparatus; and
wherein the image projector is further adapted to project onto the external surface an ancillary control image for controlling an aspect of the ancillary device; and
wherein the controller is further adapted to analyze images from the image sensor and determine if the user's finger has moved within a threshold distance of a second location on the external surface, the second location corresponding to a location at which the ancillary control image is located; wherein the controller is further adapted to report a message to the ancillary device via the port if the user's finger has moved within the threshold distance of the second location.

12. The person support apparatus of claim 11 further comprising an ambient light sensor in communication with the controller, the controller adapted to alter an intensity at which the image projector projects the first control image and the second control image onto the external surface in response to an output of the ambient light sensor.

13. The person support apparatus of claim 11 further comprising a sensor adapted to detect the presence of an authorized individual in proximity to the person support apparatus, wherein the controller is further adapted to project the first control image or the second control image when the authorized individual is in proximity to the person support apparatus and to stop projecting the first control image or the second control image when the authorized individual is not in proximity to the person support apparatus.

14. A person support apparatus comprising:
a frame;
a support adapted to support a person thereon;
a first external surface defined on a component of the person support apparatus;
a second external surface;
a first image projector positioned externally of the component and adapted to project a first image onto the first external surface such that a reflection of the first image from the first external surface is visible to a user positioned externally of the component;
a second image projector positioned externally of the component and adapted to project a second image onto the second external surface such that a reflection of the second image from the second external surface is visible to the user, the second external surface different from the first external surface;
a first image sensor positioned externally of the component and adapted to capture images of a user's finger when positioned near the first external surface;
a second image sensor positioned externally of the component and adapted to capture images of a user's finger when positioned near the second external surface;
a first controller adapted to analyze images from the first image sensor and determine if the user has moved a finger within a threshold distance of the first image; and
a second controller adapted to analyze images from the second image sensor and determine if the user has moved a finger within a threshold distance of the second image;
wherein the first and second controllers are in communication with each other, a content of the first image is received by the person support apparatus from a remote computer network, and the second image projector stops projecting the second image onto the second external surface when the user moves his or her finger within the threshold distance of a first point on the first external surface over which the first image is projected.

15. The person support apparatus of claim 14 wherein the first image includes a lockout control image that is projected onto the first point on the first external surface.

16. The person support apparatus of claim 14 wherein the second image projector projects a third image onto the second external surface when the user moves his or her finger within the threshold distance of a first point on the first external surface on which the first image is projected.

17. The person support apparatus of claim 14 wherein the person support apparatus is a bed having a footboard and a plurality of siderails and the first image projector and first image sensor are both positioned at the footboard, and the second image projector and the second image sensor are both positioned at one of the siderails.

18. The person support apparatus of claim 14 wherein the first and second controller communicate with each other over a communications network.

* * * * *